United States Patent [19]

Cardarelli et al.

[11] Patent Number: 4,511,551

[45] Date of Patent: Apr. 16, 1985

[54] METHOD AND COMPOSITION FOR THE DETECTION OF A PRECANCEROUS OR LEUKEMIC CONDITION IN MAMMALS

[75] Inventors: Nathan Cardarelli; Bernadette Cardarelli, both of Akron, Ohio

[73] Assignee: Unique Technologies, Incorporated, Mogadore, Ohio

[21] Appl. No.: 442,819

[22] Filed: Nov. 18, 1982

[51] Int. Cl.³ .................... A61K 43/00; A61K 49/00
[52] U.S. Cl. ........................................ 424/1.1; 424/9; 260/429.7; 423/89; 423/249; 423/395; 423/414; 423/544; 423/494
[58] Field of Search .................. 424/1.1, 9; 260/429.7; 423/89, 249, 395, 414, 494, 544

[56] References Cited

PUBLICATIONS

CRC Manual of Nuclear Medicine Procedures, 3rd Ed., ed. Keyes, Jr., CRC Press, 1978, pp. 86–87.
Nuclear Medicine and Biology Advances, vol. 2, (Proc. of the Third World Congress or Nuclear Medicine and Biology, Aug. 29–Sep. 2, 1982, Paris) Pergamon Press, N.Y., 1983, pp. 1366–1368.
Medical Radionuclides: Radiation Dose and Effects, U.S. Atomic Energy Commission Technical Information Center, Oak Ridge, Tenn., 1972, pp. 185–206.
Recent Advances in Nuclear Medicine, (Proceedings of the 1st World Congress of Nuclear Medicine, Sep. 30–Oct. 5, 1974, Tokyo & Kyoto, Japan), Ohkawa Printing Co., Yokohama, Japan, 1974, pp. 648–650.
Isotopes in Biochemistry and Physiology, Pt. 2, (Proceedings of the 2nd U.N. International Conference on the Peaceful Uses of Atomic Energy, Sep. 1–13, 1958, Geneva), pp. 252–257.

Primary Examiner—Christine M. Nucker
Attorney, Agent, or Firm—Oldham, Oldham & Weber Co.

[57] ABSTRACT

The invention is a method for detecting the presence of or a predisposition to cancer in mammalian individuals. A trace element, specifically tin, is administered to the individual in the form of a radioactive isotope or a compound containing a radioactive tracer. The tin-bearing compound thereafter accumulates in the various bodily organs and is excreted. Indicative of the presence of cancer or a predisposition is the lack of accumulation of the radioactive tin compound in the thymus and lymphatic system of the mammal. By comparison of the radioisotope concentration in the urine and blood, the early detection of a precancerous or leukemic condition can be made. The method is applicable to a wide variety of mammals, including human beings.

11 Claims, No Drawings

METHOD AND COMPOSITION FOR THE DETECTION OF A PRECANCEROUS OR LEUKEMIC CONDITION IN MAMMALS

TECHNICAL FIELD

The invention described herein lies in the art of cancer diagnosis. Specifically, a method is disclosed whereby the amount of accumulation of certain radioactive tin compounds in various bodily organs serves as an indication of the presence of cancer or a predisposition thereto.

BACKGROUND ART

The early diagnosis and treatment of cancer has long been the object of the scientific and medical communities. Equally useful is any method which enables the medical practitioner to single out those individuals in which the risk of developing cancer is higher than normal.

While the prior art contains numerous examples of the above, there has heretofore been no method available for diagnosis based on the distribution of trace metals in the various body organs. The instant invention provides such a method, utilizing radioactive tin.

DISCLOSURE OF INVENTION

It is accordingly an object of the invention to provide a method for detecting cancer or a predisposition to cancer in mammals.

It is another object of the invention to provide a method, as above, in which the distribution of a trace element among the body organs is used as a diagnostic indicator.

It is another object of the invention to provide a method, as above, in which the trace element is radioactive.

Still another object of the invention is to provide a method, as above, in which the trace element is administered orally in the form of a water soluble organic or inorganic compound.

Yet another object of the invention is to provide a method, as above, in which the distribution of the trace element is measured by gamma photon emission.

Still another object of the invention is to provide a method, as above, in which the trace element is radioactive tin.

BEST MODE FOR CARRYING OUT THE INVENTION

In normal, non-cancer prone mammal individuals, it has been discovered that tin bearing compounds have a propensity to circulate through the general lymphatic system with the major distribution seen in the thymus gland, spleen, and lymph nodes. By the use of a short lived gamma ray emitting tin radioisotope, which may be ingested orally, it is possible as well as desirable to determine the distribution of tin in the body. Radiography of the normal non-cancer prone, non-leukemic individual will show most or all of the ingested tin in the lymphatic system.

In cancer susceptible and/or leukemia individuals or those having cancer, the tin distribution will be small or absent in the lymphatic system with much higher quantities detected in the blood stream and the urine. The emission of gamma photons by one of several usuable tin isotopes allows the simple detection of tin distribution in the body through radiographic detection, such as radiophotography coupled with simple analysis of blood and urine for the radioisotope.

Experimental data has indicated that, when a tin material administered orally or by injection in a mammal, it accumulates in the thymus gland where it is biochemically reformed into compounds readily distributed throughout the body. The reformed tin compounds thereafter leave the thymus and are circulated throughout the body through the lymphatic system. Individual lymph nodes and the spleen, the later being well known as an accumulation point for lymphatic fluids, tend to be repositories for the tin compounds.

When the thymus gland is inoperable or atrophied, tin entering the organism is seen to bypass this organ and thus is distributed in an highly different pattern. Considerable amounts are detected in the blood stream which is the mode of circulation and only very small amounts, or none at all appear in the lymph nodes and spleen. A large quantity is metabolized, and thus metabolites containing tin are detected in the urine and feces.

As detailed in the tables given below, the accumulation of tin, or the lack thereof in the thymus provides a good indication of carcinogenic activity. There are a number of tin isotopes whose mode of radioactive decay is through emission of an easily detectable and identifiable gamma photon. Although any such isotope can be used, many have very short half-lives thus rendering quantitative detection difficult. Suitable tin isotopes include tin-110, tin-113, tin-117 and tin-119. Tin-113 is preferred due to its half-life of approximately 115 days. The radioisotope may be used in its elemental or ionic form, or as an inorganic or organic compound. The non-tin moiety or moieties used are relatively unimportant, the main requirement being that the resulting tin compound has an aqueous solubility of at least one part per million (ppm) at mammalian body temperatures.

Suitable tin compounds thus include the radioactive isotopes of tin halides having the formula:

$$Sn(X)_n$$

where X is a halo moiety selected from the group consisting of F, Cl, Br and I and n is 2 or 4 depending on whether the stannous or stannic compound is utilized. Suitable organic tin compounds include:

$$Sn(R)_n$$

where R is selected from the group consisting of alkyl and aromatic carboxylic anions having from 1 to 10 carbon atoms and n is again 2 or 4 depending on the valence of the tin cation. Another group of tin compounds include the organic halides having the formula:

$$R'_3SnX$$

where R' may be the same or different and is selected from the group consisting of alkyls having from 1 to 10 carbon atoms, phenyl and alkyl substituted phenyls having from 7 to 10 carbon atoms, and X is a halo moiety as defined above.

Of the tin halides, preferred are stannous and stannic tin chloride. Preferred carboxylic acid salts include stannous and stannic acetate. Of the organic halide compounds, preferred is tributyl tin fluoride. Again it is emphasized that the actual tin compound used is unimportant except for the above stated solubility requirement. Naturally, because the various named compounds have different solubilities, the actual amount administered to the individual will vary. In general, as the molecular weight of the tin compound increases, solubility decreases. This phenomena is well known to those skilled in the art and adjustment of dose levels to the proper amount can be achieved without undue experimentation.

In general, the amount of radioactive tin administered to the individual can vary from about 0.01 to 5.0 milligrams per kilogram of body weight. The amount is based on that of the tin isotope alone, so that when calculating the dosage, account must be taken of the total molecular weight of the tin compound.

In addition to the above named compounds, an elemental tin compound may be utilized. Further, there may be used tin salts of amino acids having the formula:

$$Sn(R'')_n$$

where R'' is a secondary or tertiary amino acid having from 1 to 10 carbon atoms, and n is 2 or 4, as above. Inorganic tin compounds, other than the halides, can also be used, such as the stannous and stannic forms of tin sulfate, nitrate and the like.

The tin compound or elemental tin may be administered in any manner known to those skilled in the art, but is preferably injected or given orally in an aqueous solution, with the oral method highly preferred. In oral administration, the route of entry into the organism is through, in a minor degree, the stomach wall and in a major degree through the small intestine wall and thereafter into the mesentary lymph nodes. Because a certain amount of time is required for the actions to commence and complete, individual should be examined at 24, 48, and preferably 72 hours after dosage.

While a whole body radiographic scan is preferred, the less complex scan of the thymus gland and spleen may suffice. The relative proportions, as evidenced by degree of gamma emission, can then be determined. A cancerous or precancerous individual will shown little thymic gamma emission and relatively low emission from spleen and the lymph nodes, the major amount of tin isotope being detected in other tissue such as the lungs, heart, muscle, fat and the like. For example, the lungs will show 10 to 100 times the gamma emission per square centimeter as seen with the thymus gland. By coupling this observation with the isotope analysis of urine and blood after 48 or more hours post dosing wherein considerable quantities are observed, the cancerous or precancerous or leukemic condition is assessed. In a non-cancerous, non-precancerous and non-leukemic individual almost all the radiation will be confined to the thymus and general lymphatic system with none or vanishingly small amounts detected in the blood or urine.

The example given below illustrates the invention by depicting the amount of tin found in three genetic strains of mice. One strain, COBS is a normal laboratory mouse which is resistant to cancer. Another strain, the AKR/KI inbred, is prone to leukemia with 80% or greater incidence. The third inbred strain is the A+ mouse which is prone to mammary tumor with an 84% or greater incidence. By comparing the various organs at set time intervals the difference in tin distribution is clearly and dramatically demonstrated. This can be seen in Table 1.

The dosage level was 0.08 milligrams of tin-113 per kilogram of mouse body weight, which is the preferred dosage level, while the dosage is desirably between about 0.05 to 1.0 milligrams per kilogram of body weight. These ranges are the same regardless of the species of individual.

Table 2 illustrates the propensity of tin to accumulate in the thymus of non-cancer prone mice, as shown by the detection of the isotope in the entire COBS cohort after 7 hours. A similar correlation can be found in Table 3 where the accumulation of isotope in the lymphatic system of the three cohorts is depicted.

Table 4 tabulates the total concentration of tin found in the lymphatic systems of the three cohorts. It is readily apparent that the cancer resistant strain accumulates tin much more readily in the lymph system than do the other strains. From Table 5 it can be seen that the radioactive label need not be on the tin atom itself. For example, Carbon-14 labelled tin compounds can be used wherein the radioactive carbon isotope emits beta radiation detectable through scintillation processes. The table shows A+ mice six weeks of age at initiation of experiment with transplanted mammary tumors and at least partially functioning thymus glands who have been drinking water with the Carbon-14 isotope of tributyl tin fluoride. The large label concentration in the thymus again illustrate the invention.

EXAMPLE

$SnCl_2$ was dissolved in water and presented orally ad libitum to cohorts of ten mice each. At the noted interval, mice were sacrificed organs removed, and the amount of gamma radiation arising from each organ measured using gamma detection instrumentation. By comparison with a standard source of 497 ppm of said radioisotope in water, and normalizing of said measurements of one gram tissue, it was possible to determine the quantity of radiolabel in each organ. Systems examined were brain, heart, lungs, stomach walls, small intestine wall, large intestine wall, kidneys, liver, femur, abdominal fat, muscle from the femur, thymus, spleen, mescentary lymph nodes, thoracic lymph node, superficial cervical lymph node, ovaries, testes, renal lymph node, blood, urine, and feces.

As the functioning of the thymus and lymphatic systems in all mammals is substantially the same, the invention can be applied to a variety of mammalian species other than mice. A major application is of course in the treatment and diagnosis of human cancer. Applications can also be found in animal husbantry, where a number of species fall victim to cancer. Thus, it will be appreciated, that while the best mode and preferred embodiments have been disclosed herein, the invention is not limited thereto or thereby. For a fuller understanding of the scope of the invention, reference should therefore be made to the attached claims.

TABLE 1

| Organ | COBS Cancer Resistant | AKR Leukemia Prone | A+ Mammary Tumor Prone |
|---|---|---|---|
| | 24-Hour Results: Averaged | | |
| Thymus | 149 ppm | 0.9 ppm | 2.4 ppm |
| Blood | 0.0 ppm | 20.2 ppm | 46.0 ppm |
| Urine | 2.7 ppm | 8.5 ppm | 15.0 ppm |
| Heart | 2.1 ppm | 3.8 ppm | 6.4 ppm |
| Spleen | 55 ppm | 20.7 ppm | 46.7 ppm |
| Thoracic Nodes | 129 ppm | 3.9 ppm | 16.9 ppm |
| Lungs | 6.5 ppm | 4.7 ppm | 17.0 ppm |

TABLE 1-continued

| Organ | COBS Cancer Resistant | AKR Leukemia Prone | A+ Mammary Tumor Prone |
|---|---|---|---|
| Liver | 6.5 ppm | 2.6 ppm | 3.6 ppm |
| Kidney | 2.1 ppm | 0.6 ppm | 5.9 ppm |
| 48-Hour Results: Averaged | | | |
| Thymus | 122 ppm | 0.0 ppm | 1.0 ppm |
| Blood | 0.6 ppm | 18.9 ppm | 14.9 ppm |
| Urine | 1.2 ppm | 8.2 ppm | 2.9 ppm |
| Heart | 0.9 ppm | 8.3 ppm | 0.6 ppm |
| Spleen | 49 ppm | 6.4 ppm | 2.5 ppm |
| Thoracic Nodes | 119 ppm | 9.3 ppm | 14.3 ppm |
| Lungs | 1.0 ppm | 3.5 ppm | 1.7 ppm |
| Liver | 0.4 ppm | 1.4 ppm | 1.3 ppm |
| Kidney | 0.4 ppm | 8.9 ppm | 5.9 ppm |
| 72-Hour Results: Averaged | | | |
| Thymus | 118 ppm | 11.7 ppm | 3.8 ppm |
| Blood | 0.9 ppm | 26.8 ppm | 5.2 ppm |
| Urine | 3.8 ppm | 0.6 ppm | 18.2 ppm |
| Heart | 1.6 ppm | 6.2 ppm | 11.5 ppm |
| Spleen | 57 ppm | 13.6 ppm | 7.0 ppm |
| Thoracic Nodes | 127 ppm | 3.7 ppm | 73 ppm |
| Lungs | 8.2 ppm | 0.9 ppm | 2.2 ppm |
| Liver | 1.2 ppm | 0.7 ppm | 1.6 ppm |
| Kidney | 4.6 ppm | 1.6 ppm | 3.6 ppm |

TABLE 2

Gamma Radiation From Thymus Arising from Tin-113

| Post Exposure Time | COBS Number Examined | COBS Number + | A+ Number Examined | A+ Number + | AKR Number Examined | AKR Number + |
|---|---|---|---|---|---|---|
| 0 (control) | 10 | 0 | 10 | 0 | 10 | 0 |
| 3 hrs | 11 | 2 | 10 | 1 | 10 | 0 |
| 5 hrs | 10 | 6 | 10 | 2 | 10 | 3 |
| 7 hrs | 10 | 10 | 10 | 2 | 10 | 2 |
| 9 hrs | 10 | 10 | 10 | 1 | 10 | 2 |
| 12 hrs | 10 | 10 | 10 | 2 | 10 | 0 |
| 16 hrs | 10 | 10 | 10 | 4 | 10 | 3 |
| 24 hrs | 10 | 10 | 20 | 3 | 10 | 1 |
| 48 hrs | 10 | 10 | 13 | 5 | 10 | 0 |
| 72 hrs | 10 | 10 | 10 | 2 | 10 | 3 |

Note: + = presence of $^{113}$Sn.

TABLE 3

Tin-113 Accumulation in the Spleen and Lymphatic System

Tin-113 Content in PPM

| Post Exposure Time | COBS $M^1$ | COBS $R^2$ | COBS $SC^3$ | COBS $TH^4$ | COBS $S^5$ | A+ M | A+ R | A+ SC | A+ TH | A+ S | AKR M | AKR R | AKR SC | AKR TH | AKR S |
|---|---|---|---|---|---|---|---|---|---|---|---|---|---|---|---|
| 24 hrs | 82 | 197 | 141 | 129 | 55 | 20 | 46 | 11 | 17 | 46 | 3 | 2 | 7 | 4 | 20 |
| 48 hrs | 90 | 132 | 121 | 119 | 49 | 9 | 1 | 5 | 14 | 2 | 13 | 8 | 17 | 9 | 6 |
| 72 hrs | 93 | 115 | 119 | 127 | 57 | 36 | 38 | 9 | 7 | 7 | 8 | 12 | 8 | 4 | 14 |

Note:
[1] Mesentary lymph nodes
[2] Renal lymph nodes
[3] Superficial cervical node
[4] Thoracic node
[5] Spleen

TABLE 4

Concentration of Tin-113 in the Lymphatic System as Compared to all Organ Systems from the Enumerated List

| Post Exposure Time | COBS | A+ | AKR |
|---|---|---|---|
| 12 hrs | 95.9% | 50.5% | 49.3% |
| 24 hrs | 94.8% | 55.3% | 23.9% |
| 48 hrs | 94.8% | 39.1% | 51.5% |
| 72 hrs | 95.8% | 72.9% | 38.3% |

TABLE 5

Analysis by Liquid Scintillation of $^{14}$C Label in A+ Tumor Transplanted Mouse Tissue

| Organ | Average Organ $^{14}$C Concentration | Concentration Range |
|---|---|---|
| Blood | 10 ppb | 0–31 ppb |
| Heart | 17 | 0–46 |
| Liver | 8 | 0–17 |
| Brain | 15 | 3–24 |
| Kidney | 17 | 4–21 |
| Fat | 23 | 16–33 |
| Thymus | 493 | 81–1391 |
| Spleen | 52 | 10–128 |
| Lung | 10 | 0–41 |
| Small intestine | 13 | 3–17 |
| Large intestine | 13 | 4–19 |
| Stomach | 36 | 24–40 |
| Tumor | 11 | 0–21 |

What is claimed is:

1. A diagnositic method for determining the presence of or predisposition to cancer in a mammel comprising:
   providing a radioactive isotope of tin;
   administering said isotope to a mammalian individual; and
   thereafter measuring the accumulation of said isotope in the body of said individual by gamma emission;
   wherein the lack of accumulation of said isotope in the lymphatic system and the thymus indicates the presence of or predisposition to cancer in said individual.

2. A method according to claim 1, wherein accumulation of said isotope in the blood and urine indicates the presence of or predisposition to cancer in said individual.

3. A method according to claim 2, wherein said isotope of tin is in the form of a compound selected from the group consisting of:

$Sn(X)_n$ where n may be 2 or 4 and X is fluorine chlorine, bromine or iodine, $Sn(R)_n$ where n may be 2 or 4 and R may be the same or different and is selected from the group consisting of alkyl and aromatic carboxylic anions having from 1 to 10 carbon atoms, $R'_3SnX$ where R' may be the same or different and is selected from the group consisting of alkyls having from 1 to 10 carbon atoms, $Sn^o$, $Sn(R'')_n$ where n is 2 or 4 and R'' is the same or different and is selected from the group consisting of secondary or tetiary amino acid moieties having from 1 to 10 carbon atoms, $Sn(SO_4)_2$, $SnSO_4$, and $Sn(NO_3)_n$ PS
where n is 2 or 4.

4. A method according to claim 3, wherein said isotope is selected from the group consisting of tin-110, tin-113, tin-117 and tin-119.

5. A method according to claim 4, wherein said isotope is administered orally to said mammal in an amount of from about 0.01 to about 5 milligrams per kilogram of body weight.

6. A method according to claim 5, wherein said isotope of tin is tin-113.

7. A method according to claim 6, wherein said mammalian individual is a mouse.

8. A method according to claim 6, wherein said mammalian individual is a human being.

9. A diagnostic method for determining the presence of or predisposition to cancer in a mammal, comprising:
providing a radioactive tin-containing compound in which one or more of the non-tin atoms in said compound are radioactive;
administering said compound to a mammalian individual; and
thereafter measuring the accumulation of said compound in the body of said individual through a scintillation process;
wherein the lack of accumulation of said compound in the lymphatic system in the thymus indicates the presence of or predisposition to cancer in said individual.

10. A method according to claim 9, wherein the accumulation of said compound in the blood and urine of said individual indicates the presence of predisposition to cancer in said individual.

11. A method according to claim 10, wherein said mammalian individual is a human being.

* * * * *